United States Patent
Bronshtein (10) Patent No.: US 6,509,146 B1
(45) Date of Patent: Jan. 21, 2003

(54) SCALABLE LONG-TERM SHELF PRESERVATION OF SENSITIVE BIOLOGICAL SOLUTIONS AND SUSPENSIONS

(75) Inventor: Victor Bronshtein, Penfield, NY (US)

(73) Assignee: Universal Preservation Technologies, Inc., Rochester, NY (US)

( * ) Notice: Subject to any disclaimer, the term of this patent is extended or adjusted under 35 U.S.C. 154(b) by 0 days.

(21) Appl. No.: 08/979,458

(22) Filed: Nov. 26, 1997

Related U.S. Application Data (63) Continuation-in-part of application No. 08/785,472, filed on Jan. 17, 1997, now abandoned, which is a continuation-in-part of application No. 08/785,473, filed on Jan. 17, 1997, now Pat. No. 5,766,520.

(60) Provisional application No. 60/018,573, filed on May 29, 1996, and provisional application No. 60/021,796, filed on Jul. 15, 1996.

(51) Int. Cl.$^7$ .............................. A01N 1/00; A01N 1/02

(52) U.S. Cl. ......................................................... 435/1.3

(58) Field of Search ........................................ 435/1.3

(56) References Cited

U.S. PATENT DOCUMENTS

| | | |
|---|---|---|
| 4,215,153 A | 7/1980 | Kai et al. |
| 4,396,563 A | 8/1983 | Gusmer |
| 4,451,569 A | 5/1984 | Kobayashl et al. |
| 4,559,298 A | 12/1985 | Fahy |
| 4,642,903 A | 2/1987 | Davies et al. |
| 4,891,319 A | 1/1990 | Roser |
| 5,026,566 A | 6/1991 | Roser |
| 5,030,469 A | 7/1991 | Mergelsberg |
| 5,039,540 A | 8/1991 | Ecanow et al. |
| 5,079,018 A | 1/1992 | Ecanow et al. |
| 5,084,101 A | 1/1992 | Engles et al. |
| 5,149,653 A | 9/1992 | Roser |
| 5,190,987 A | 3/1993 | Parkinson |
| 5,200,399 A | 4/1993 | Wettlaufer et al. |
| 5,250,429 A | 10/1993 | Jolly et al. |
| 5,252,620 A | 10/1993 | Elliott et al. |
| 5,290,582 A | 3/1994 | Dressel et al. |
| 5,354,558 A | 10/1994 | Britton et al. |
| 5,425,951 A | 6/1995 | Goodrich, Jr., et al. |
| 5,439,945 A | 8/1995 | Smies |
| 5,565,318 A | 10/1996 | Walker et al. |
| 5,597,416 A | 1/1997 | Fuisz et al. |
| 5,621,094 A | 4/1997 | Roser |
| 5,648,206 A | 7/1997 | Goodrich, Jr. et al. |
| 5,762,961 A * | 6/1998 | Roser et al. ............... 424/464 |
| 5,766,520 A | 6/1998 | Bronshtein |

FOREIGN PATENT DOCUMENTS

| | | |
|---|---|---|
| RU | 959786 | 9/1982 |
| WO | W O 9314191 | 7/1993 |
| WO | W O 9640077 | 12/1996 |

OTHER PUBLICATIONS

Burke, Michael J.; "The Glassy State and Survival of Anhydrous Biological Systems," (1986), In A.C. Leopold, ed, "Membranes Metabolism and Dry Organisms." Cornell University Press, Ithaca, NY, pp. 358–364.

Harris, R.J.C.; "Biological Applications of Freezing and Drying," Academic Press Inc., NY (1964) pp. 87, 124, 125, 151, 163.

Rogers, L.A.; "The Preparation of Dried Cultures," Circular 171, U.S. Dept. of Agric., Bureau of Animal Industry, Washington, 1911, pp. 101–123.

Schoppet, E.F., et al.; "Continuous Vacuum Drying of Whole Milk Foam IV Pilot Plant," Journal of Dairy Science, vol. 53, No. 1, Jan., 1970, pp. 56–62.

Annear, "Preservation of Leptospiræ by drying" J. Path. Bact. vol. 72, pp. 322–323, 1956.

Annear, "Observations of the Preservation by Drying of Leotospirae and Some Other Bacteria", Austral. J. Exp. Biol. vol. 36, pp. 1–4., 1958.

Annear, "Observation on Drying Bacteria from the Frozen and From the Liquid State" Austral. J. Exp. Biol. vol. 36, pp. 211–221, 1958.

Annear, "Recovery of *Strigomonas oncopeltii* after Drying From the Liquid State" Aust. J. Exp. Biol., vol. 39, pp. 295–303, 1961.

Annear, "Preservation of the Reiter Treponeme by Drying From the Liquid State", J. Bact., vol. 83, pp. 932–933, 1962.

Annear, "The Preservation of Leptospires by Drying From the Liquid State", J. Gen. Microbiol., vol. 27, pp. 341–343, 1962.

Annear, "Recoveries of Bacteria After Drying on Cellulose Fibres A Method for The Routine Preservation of Bacteria", Austral. J. Exp. Biol., vol. 40, pp. 1–8, 1962.

Annear, "Preservation of Yeast by Drying", Austral. J. Exp. Biol., vol. 41, pp. 575–580., 1963.

Annear, "Recoveries of Bacteria After Drying In Glutamate and Other Substances", Aust. J. exp. Biol. Med. Sci., vol. 42, pp. 717–722, 1964.

Annear, Recoveries of Bacteria After Drying *in Vacuo* at a Bath Temperature of 100°C., Nature, No. 5050, p. 761, Aug. 13, 1966.

Annear, Survival of Bacteria in Desiccates at 100°C in Dry Atmospheres, Nature vol. 206 No. 4991, pp. 1373–1374, Jun. 26, 1965.

\* cited by examiner

*Primary Examiner*—Jon P. Weber
(74) *Attorney, Agent, or Firm*—Knobbe, Martens, Olson & Bear, LLP (57) ABSTRACT

This invention discloses methods for the long-term preservation of industrial scale biological solutions and suspensions containing biologically active molecules, cells and small multicellular specimens at ambient temperatures by dehydration in amorphous very viscous liquid or glass state. The scale up method comprises the primary drying step of boiling under vacuum to form a mechanically-stable foam and a secondary drying step to increase the stability. Vitrification can subsequently be achieved by cooling the dried material to the storage temperature which is lower than the glass transition temperature.

6 Claims, 6 Drawing Sheets

SCALABLE LONG-TERM SHELF PRESERVATION OF SENSITIVE BIOLOGICAL SOLUTIONS AND SUSPENSIONS

RELATED APPLICATIONS

This is a continuation-in-part of patent application Ser. No. 08/785,472, filed on Jan. 17, 1997, which claims priority under § 119(e) to Provisional Application No. 60/018,573, filed on May 29, 1996 now abandoned. This is also a continuation-in-part of patent application Ser. No. 08/785,473, filed Jan. 17, 1997, now U.S. Pat. No. 5,766,520, which claims priority under § 119(e) to Provisional Application No. 60/021,796, filed on Jul. 15, 1996 now abandoned.

BACKGROUND OF THE INVENTION

This invention relates to methods for preserving solutions and suspensions containing biologically active molecules, viruses (vaccines), cells, and small multicellular specimens. More particularly, the invention relates to methods for long-term storage of these labile biological materials at ambient temperatures in dehydrated, very viscous amorphous liquid or glass state.

The preservation and storage of solutions or suspensions of biologically active materials, viruses, cells and small multicellular specimens is important for food and microbiological industries, agriculture, medical and research purposes. Storage of dehydrated biologically active materials carries with it enormous benefits. Dehydrated reagents, materials and cells have reduced weight and require reduced space for storage, notwithstanding their increased stability.

Suggestions in the prior art for providing enhanced-stability preparations of labile biological materials in dehydrated form include freeze-drying and vacuum or air-drying. While freeze-drying methods are scalable to industrial quantities, materials dried by such methods can not be stored at ambient temperatures for long periods of time. In addition, the freezing step of freeze-drying is very damaging to many sensitive biological materials. Alternatively, vacuum and air-drying methods do not yield preparations of biological materials which are scalable to industrial quantities and stable for extended periods of time at ambient temperatures, because destructive chemical reactions may continue to proceed in such dried preparations.

Some of the problems associated with preservation by freezing and drying have been addressed by addition of protectant molecules, especially carbohydrates, which have been found to stabilize biological materials against the stresses of freezing and drying. However, despite the presence of protectants, the long-term stability may still require low temperature storage, in order to inhibit diffusion-dependent destructive chemical reactions. Thus, further innovations have been sought to provide long-term storage of labile biological materials at ambient temperatures.

Storage of dried materials at ambient temperatures would be cost effective when compared to low temperature storage options. Furthermore, ambient temperature storage of biological materials such as vaccines and hormones would be extremely valuable in bringing modern medical treatments to third world countries where refrigeration is often not available. As the many benefits of shelf preservation of biological specimens have come to be appreciated, researchers have endeavored to harness vitrification as a means of protecting biological materials against degradative processes during long-term storage. Consequently, this technology of achieving the "glass" state, has been anticipated to emerge as a premier preservation technique for the future.

A glass is an amorphous solid state which may be obtained by substantial undercooling of a material that was initially in the liquid state. Diffusion in vitrified materials, or glasses, occurs at extremely low rates (e.g. microns/year). Consequently, chemical or biological changes requiring the interaction of more than one moiety are practically completely inhibited. Glasses normally appear as homogeneous, transparent, brittle solids, which can be ground or milled into a powder. Above a temperature known as the glass transition temperature (Tg), the viscosity drops rapidly and the glass becomes deformable and the material turns into a fluid at even higher temperatures. The optimal benefits of vitrification for long-term storage may be secured only under conditions where Tg is greater than the storage temperature. The Tg is directly dependent on the amount of water present, and may therefore be modified by controlling the level of hydration; the less water, the higher the Tg.

Unfortunately, the advantages of vitrification technology as a means of conferring long-term stability to labile biological materials at ambient temperatures have not been fully utilized. Current methods of ambient temperature preservation by drying are designed for laboratory processing of very small quantities of materials. Consequently, such methods are not compatible with large scale commercial operations. Other technical problems related to monitoring of the glass transition temperature have also posed obstacles to the commercial development. Thus, while drying and vitrification technology are potentially attractive as scalable methods for long-term storage of biological materials, problems remain to be overcome before the advantages of storage in the glass state can be commercially exploited.

SUMMARY OF THE INVENTION

A method is disclosed for preserving industrial quantities of solutions and suspensions containing sensitive biological materials comprising drying the samples by boiling under vacuum in a temperature range of −15° C. to 70° C. A mechanically-stable foam, consisting of thin amorphous films of concentrated solutes is formed. Such foams will not collapse for a least one hour at −20° C. when stored under vacuum. To increase the stability, the foams can be further dried for at least 12 more hours under vacuum at temperatures ranging from 0° to 100° C., wherein the drying temperature is greater than the desired storage temperature, selected from within the range of 0° to 70° C.

To provide long-term shelf preservation of biological solutions and suspensions in the glass state, the mechanically-stable foams may be subjected to secondary drying under vacuum in the range of 0° to 100° C. for a period of time sufficient to increase the glass transition temperature to a point above the selected storage temperature within the range of 0° to 70° C. Finally, a composition is disclosed for protecting cells and viruses during the recited drying and vitrification processes, comprising a non-reducing monosaccharide, a dissacharide (like sucrose) and a biological polymer.

DETAILED DESCRIPTION OF THE INVENTION

In attempting to develop vitrification as a means of preserving biological materials at ambient or higher temperatures, the Applicant discovered that certain theoretical limitations which underlie vitrification processes have not been fully appreciated. As a result, many vitrification methods claimed in the prior art embody technical defects which have hindered or misled efforts directed at harnessing the advantages of vitrification in the biomedical and pharmaceutical industries. There are several potential reasons for the defects in many prior art vitrification methods. First, while the standard method for determining Tg, differential scanning calorimetry ("DSC"), is reliable for simple sugars and mixtures thereof, it is unreliable for solutions of polymeric substances, like Ficoll and hydroxyethyl starch, which are frequently employed to stabilize biological samples. Indeed, the applicant recently presented evidence at the Society of Cryobiology meeting 1997, that the changes in specific heat are very small (undetectable by DSC) in concentrated solutions of hydroxyethyl starch, occurring over a wide temperature range in dried samples. Consequently, for practical purposes, the phase change in polymeric materials is undetectable by DSC.

FIG. 1 shows a comparison of DSC scans (conducted at 2°/min) for a 1:1 mixture of sucrose and raffinose (left panels) after secondary drying for 5 days at room temperature (A) and 70° C. (B) with those DSC results obtained for Ficoll (right panels), dried for 5 days at room temperature (C) and 70° C. (D). The Tg for sucrose-raffinose was determined by reference to the point of inflection, which is clearly discernable. The Tg for sucrose-raffinose increased dramatically with the drying temperature from 1.86° C. following room temperature drying to 59.71° C. following drying at 70° C. In contrast, there is no clearly discernable inflection point for Ficoll, shown in FIG. 1 (C & D). Thus, estimation of Tg by DSC in biological samples dehydrated in the presence of polymeric protectants, like Ficoll, is unreliable.

Another technical limitation in vitrification methods, which appears not to have been widely appreciated, is that dehydration is a process limited by diffusion of water molecules. As a sample is dried, diffusion and consequently dehydration slow as the sample becomes more viscous and virtually stop as transition into the glass state is approached. Accordingly, no further dehydration is possible. Likewise, since Tg depends on the level of dehydration achieved, no further increase in Tg is possible. It is therefore technically impossible at constant hydrostatic pressure to achieve a Tg of greater than the dehydration temperature. Consequently, the glass state can be entered only upon subsequent cooling. Thus, prior art references which disclose drying at X° C. to obtain a Tg of greater than X° C. are impossible and are probably based upon erroneous measurements of Tg by DSC.

Figure 1A:
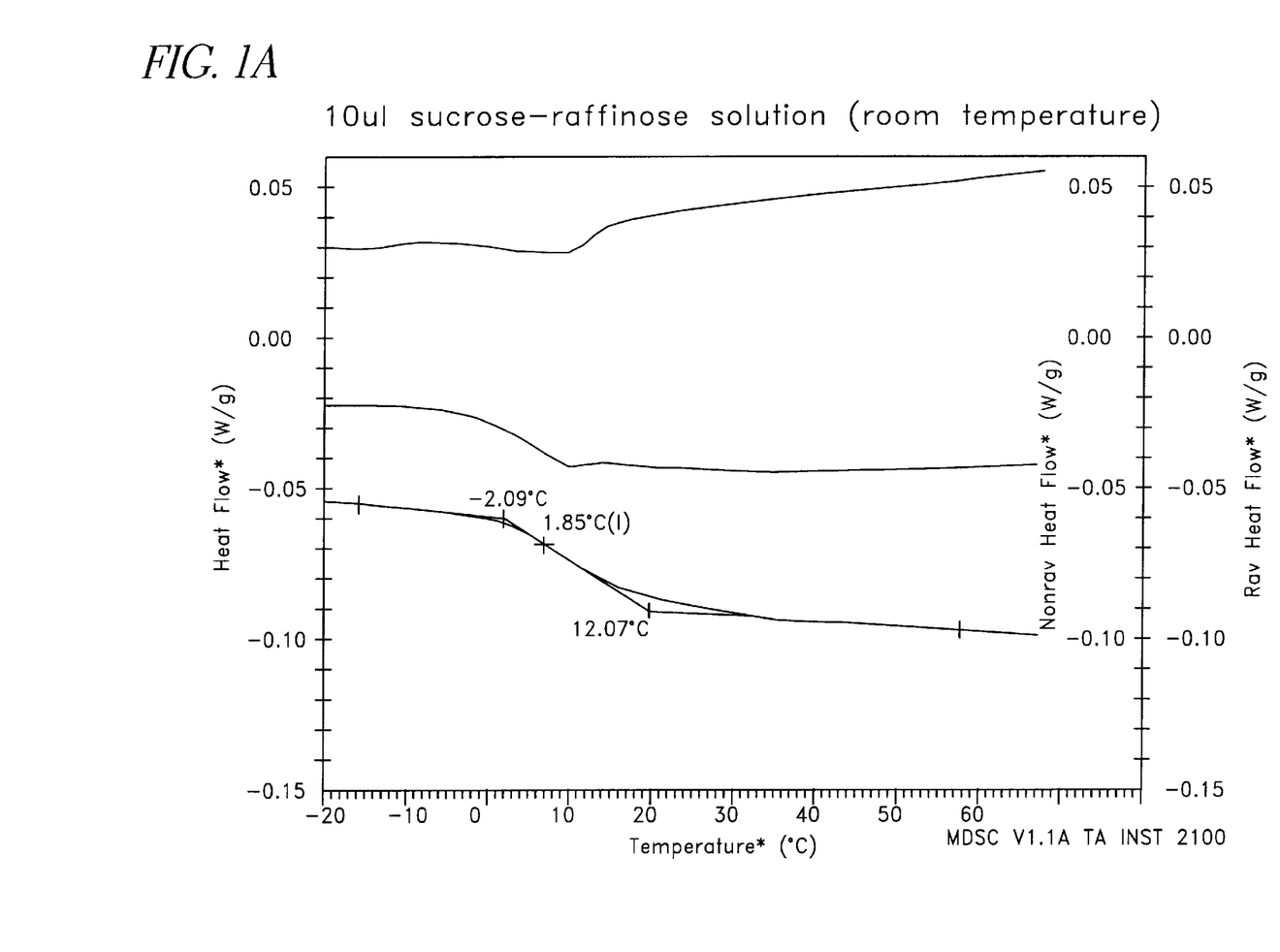
FIG. 1 depicts a DSC scan of a mixture of sucrose and raffinose (A & B) and Ficoll (C & D).
Figure 1B:
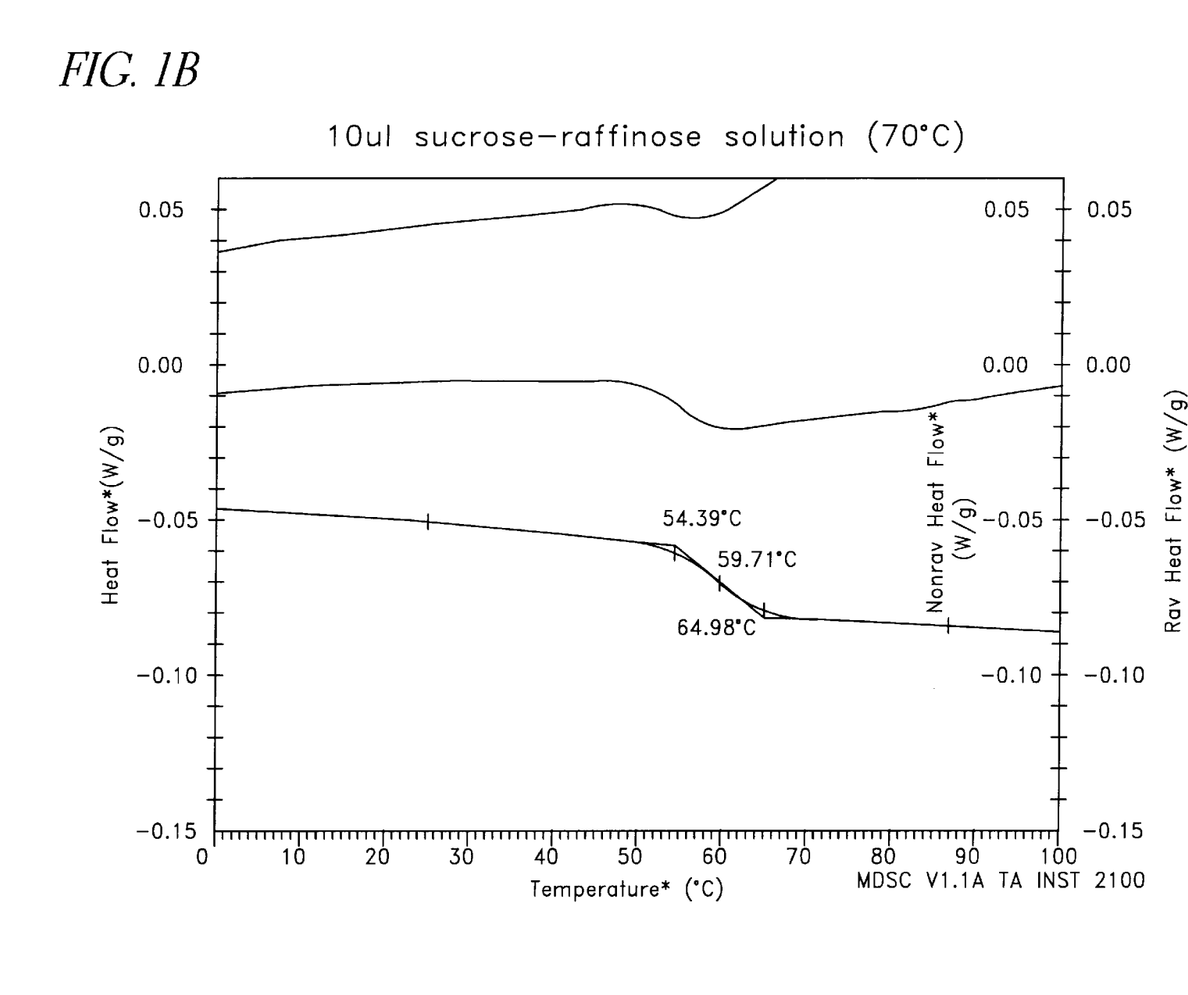
Figure 1C:
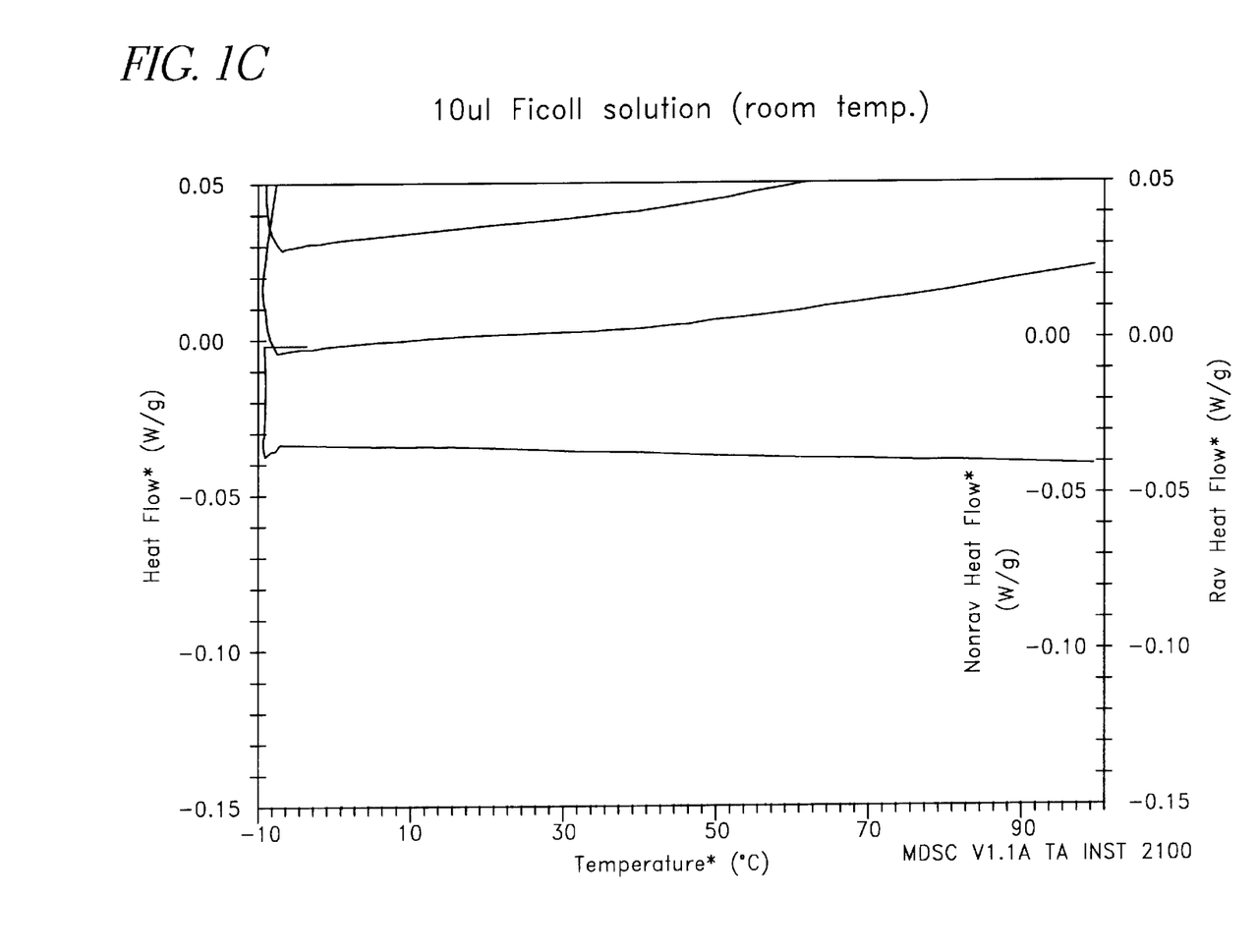
Figure 1D:
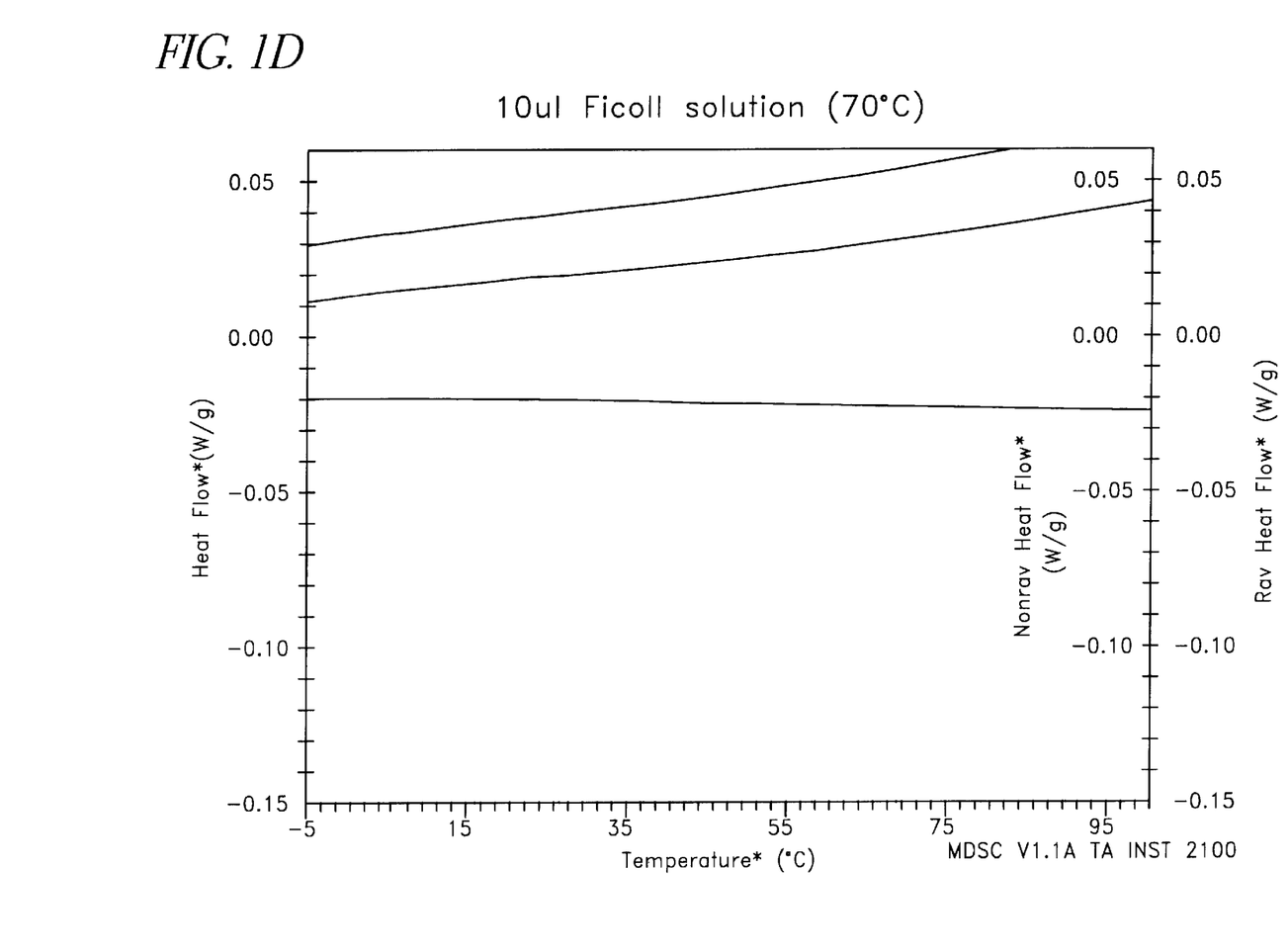
Figure 2:
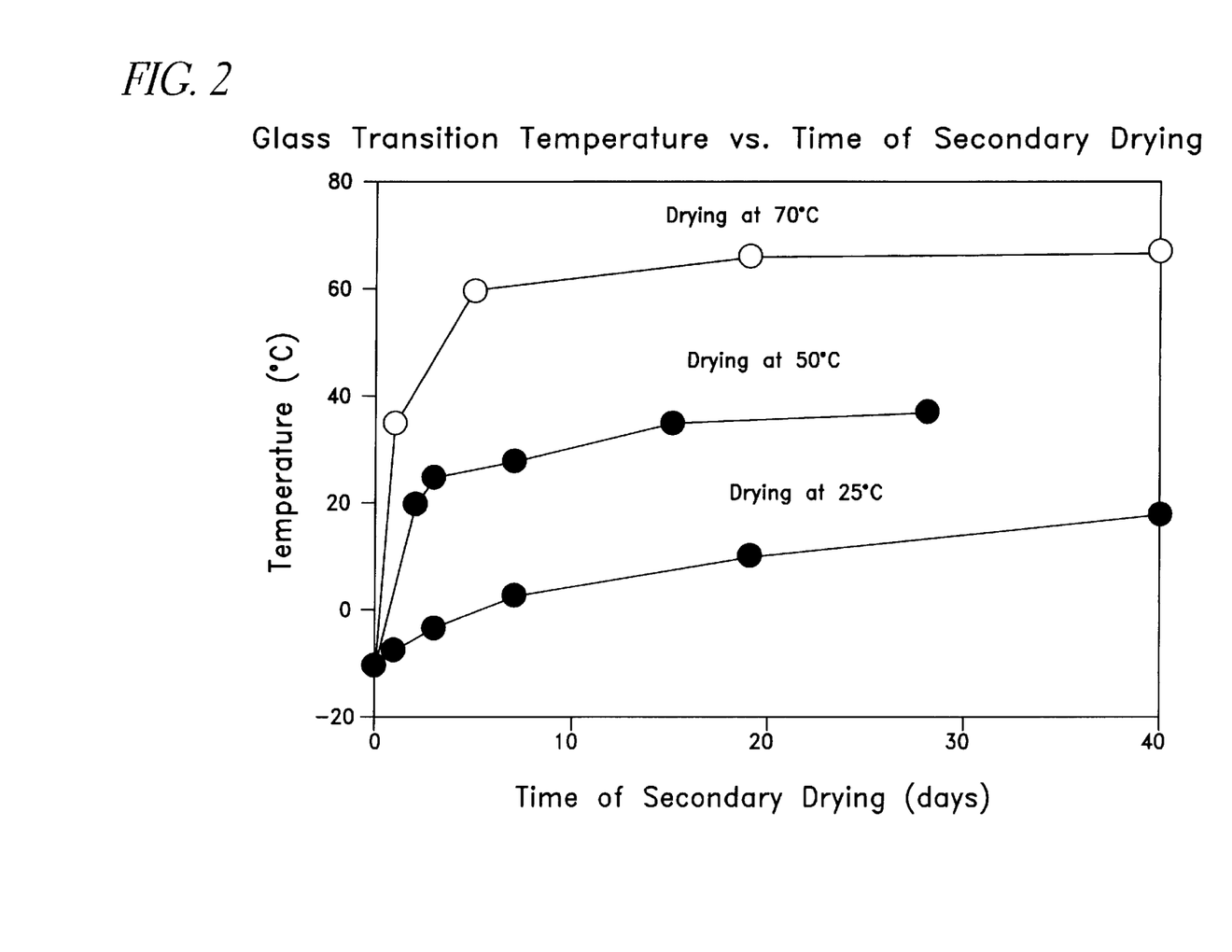
FIG. 2 is a graph depicting the relationship between Tg and dehydration time at three different temperatures.

While many prior art methods have purported to achieve the glass state at ambient storage temperatures (i.e. Tg >20°–30° C.), it is evident from the relatively short dehydration periods and low dehydration temperatures that such disclosures in fact embody defects in theoretical reasoning and empirical methods which preclude true vitrification. At best, these methods achieve a very viscous liquid state, but no glass state could ever emerge. To illustrate the inoperability of prior art methods, FIG. 2 depicts the dependence of Tg on secondary drying time at three different temperatures. Solutions (10 ul) of a 1:1 mixture of sucrose and raffinose were initially dried under vacuum overnight at room temperature, followed by secondary drying at the indicated temperatures; Tg was determined by DSC, which is reliable for simple sugar mixtures. Because Ficoll is a sucrose polymer, it is reasonable to infer that the conditions required to raise Tg in sucrose would be similar in a Ficoll solution having an equivalent sucrose concentration. Clearly, Tg is never greater than the drying temperature. For example, secondary drying times should be greater than 12 hours, even at 70° C., in order for Tg to approach room temperature (FIG. 2).

Another technical limitation not generally appreciated, but of critical importance to the commercial exploitation of vitrification, is that the time of drying is inversely proportional to the diffusion coefficient of water and proportional to the square of the sample size. Consequently, dehydration of a 10 microliter spherical drop of a sucrose-raffinose mixture at 70° C. required more than 12 hours to attain a Tg of greater than 25° C. (see FIG. 2). However, it would take more than 55 hours for a 100 microliter sample and 258 hours for a 1 ml sample, at 70° C. to reach the same Tg. Similarly, dehydration of a 10 microliter sample of sucrose-raffinose at 50° C. required more than 2 days to raise the Tg above room temperature. But it would take more than 9 days for a 100 microliter sample and 43 days for a 1 ml sample. Thus, limitations on sample size have tended to impede large scale commercial development of vitrification technology.

Among the commercial attempts at harnessing the advantages of vitrification, Walker et al. (U.S. Pat. No. 5,565,318) describes a method for making a reagent semi-sphere comprising at least one biologically active reagent and a glass-forming filler material, such as carbohydrates, carbohydrate derivatives, mixtures of sugars, and proteins, preferably the Ficoll polymer. An apparent "glassy, porous composition" is achieved by dehydration of emulsion droplets under reduced atmosphere at temperatures of 10° to 50° C. for periods of time from 1 to 4 hours, preferably 1 hour at 10° C., 300 Torr. While, Walker provides that other drying profiles (time and temperature ranges) can be employed as long as a Tg of between 30° and 45° C. is attained, the method is inoperable because a Tg of 30° C. could never be achieved with dehydration at 10° C. (see FIG. 2); the erroneously elevated Tg was determined in Walker by DSC in samples dried in a Ficoll-based storage medium. Thus, while Walker discloses storage of biological samples in a vitrified state, this reference failed to recognize or overcome the theoretical constraints and technical difficulties of vitrification processes.

Similarly, Jolly et al. (U.S. Pat. No. 5,250,429) claims a specific application of vitrification technology to the preservation of restriction enzymes. This method for making the glassified composition comprising a carbohydrate stabilizer, preferably Ficoll, and a restriction enzyme involves dehydration in a vacuum, overnight at room temperature, followed drying for an additional 2 hours at 50° C. The final "glassified" composition has a preferred Tg of at least 30° C., and a storage temperature of 20° C. Here again, the brief incubation at 50° C. disclosed by this reference would be insufficient to raise the Tg above room temperature.

Franks et al. (U.S. Pat. No. 5,098,893) describes a vitrification method for rendering biological materials storage stable at room temperature. An apparent "glassy amorphous state" is produced by dehydrating a mixture comprising a carbohydrate carrier substance and at least one material to be stored. Several vitrification protocols are disclosed. Preferably, an initial drying incubation is conducted under vacuum at temperatures between 20° and 30° C. for 24 to 36 hours. Subsequently, after the Tg has been sufficiently elevated (determined by DSC to be above 30° C.), a second evaporation is carried out at 40° to 70° C. for 2 hours. The Tg of at least 30° C. is sufficient to allow stable storage at room temperature (20° C.). Unfortunately, Franks et al., like Jolly et al., were misled by the DSC measurements of dried polymers and markedly underestimated the amount of drying time at elevated temperatures sufficient to produce a Tg above room temperature (see FIG. 2).

The vitrification method of the present invention, used in preserving biological specimens, comprises a primary drying step, a secondary drying step, whereby the resulting dehydration at temperatures above the selected storage temperature is sufficient to increase Tg to a point above the desired storage temperature, and cooling the dried material to the storage temperature to achieve vitrification. The addition of an initial step of forming a mechanically-stable porous structure, by boiling the sample under reduced atmosphere of less than about 4 Torr, facilitates scale-up of the preservation method to process large volumes of biological materials. Furthermore, application of the Thermally Stimulated Depolarization Current ("TSDC") technique designed for measurements of Tg in polymeric materials, permits reliable monitoring of vitrification processes in biological materials stabilized using sugar polymers. Thus, the method of this invention yields dried biological materials in the glass state, having Tg's above the selected storage temperatures, thereby enabling long-term shelf preservation of these labile materials.

Biologically active materials which can be preserved by the present methods include, without limitation, biological solutions and suspensions containing peptides, proteins, antibodies, enzymes, co-enzymes, vitamins, serums, vaccines, viruses, liposomes, cells and certain small multi-cellular specimens. Dehydration of biological specimens at elevated temperatures may be very damaging; for example, if the temperatures used are higher than the applicable protein denaturation temperature. To protect the samples from the damage associated with elevation of temperature, the dehydration process may be performed in steps. Primary dehydration should be performed at temperatures which are sufficiently low to permit the dehydration without loss of biological activity. If dehydration at sub-zero temperatures is preferred, one may apply dehydration from a partially frozen state under vacuum. Alternatively, if the samples are stable at higher temperatures, then vacuum or air-drying techniques could be employed.

A variety of polyols and polymers are known in the art and may serve as protectants as long as they enhance the ability of the biologically active material to withstand drying and storage and do not interfere with the particular biological activity. Indeed, the protectant molecules provide other advantages during preservation (see infra, as an aid to foaming) besides stabilizing biological materials during dehydration. These include, without limitation, simple sugars, such as glucose, maltose, sucrose, xylulose, ribose, mannose, fructose, raffinose, and trehalose, carbohydrate derivatives, like sorbitol, synthetic polymers, such as polyethylene glycol, hydroxyethyl starch, polyvinyl pyrrolidone, polyacrylamide, polyethyleneimine, and sugar copolymers, like Ficoll and Dextran, and combinations thereof. Proteins may also serve as protectants.

In one embodiment of the present invention, where cells or viruses are being preserved, the protective composition may further comprise mixtures of: a low molecular weight sugar, a dissaccharide, and a high molecular weight biological polymer. The low molecular weight sugar is used to penetrate and protect intracellular structures during dehydration. The low molecular weight, permeating sugars may be selected from a variety of ketoses, which are non-reducing at neutral or higher pH, or methylated monosaccharides. Among the non-reducing ketoses, are included: the six carbon sugars, fructose, sorbose, and piscose; the five carbon sugars, ribulose and xylulose; the four carbon sugar, erythrulose; and the three carbon sugar, 1,3 dihydroxydimethylketone. Among the methylated monosaccharides, are the alpha and beta methylated forms of gluco, manno, and galacto pyranoside. Among the methylated five carbon compounds are the alpha and beta forms of arabino and xylo pyranosides. Disaccharides, like sucrose, are known to be effective protectants during desiccation because they replace the water of hydration on the surface of biological membranes and macromolecules. In addition, the Applicant found that when dried under vacuum, sucrose may be effectively transformed into a stable form, composed of thin amorphous films of the concentrated sugar.

The Applicant also found that combining a low molecular weight non-reducing sugar, like fructose, with disaccharides, like sucrose, effectively prevents crystallization of the dissaccharide during dehydration. Finally, a polymer is employed to increase the glass transition temperature of the mixture, which may be decreased by inclusion of the low molecular weight monosaccharides. All biological polymers which are highly soluble in concentrated sugar solutions will work. For example, polysaccharides, like Ficoll, and Dextran, and synthetic polymers, like hydroxyethyl starch, polyethylene glycol, polyvinyl pyrrolidone, polyacrylamide, as well as highly soluble natural and synthetic biopolymers (e.g. proteins) will help to stabilize biological membranes and increase Tg.

To facilitate scaling up of the drying and vitrification methods, the primary drying step preferably involves the formation of a mechanically-stable porous structure by boiling under a vacuum. This mechanically-stable porous structure,. or "foam," consists of thin amorphous films of the concentrated sugars. Such foams will not collapse for at least 1 hour while maintained at −20° C. under vacuum. More preferably, the mechanically-stable foams will not collapse for at least 3 days when stored at temperatures up to 70° C. under vacuum. Foam formation is particularly well suited for efficient drying of large sample volumes, before vitrification, and as an aid in preparing an easily divisible dried product suitable for commercial use. Preferably, before boiling under vacuum, the dilute material is concentrated by partially removing the water to form a viscous liquid. This concentration can be accomplished by evaporation from liquid or partically frozen state, reverse osmosis, other membrane technologies, or any other concentration methods known in the art. Alternatively, some samples may be sufficiently viscous after addition of the sugar protectants. Subsequently, the reduced/viscous liquid is further subjected to high vacuum, to cause it to boil during further drying at temperatures substantially lower than 100° C. In other words, reduced pressure is applied to viscous solutions or suspensions of biologically active materials to cause the solutions or suspensions to foam during boiling, and during the foaming process further solvent removal causes the ultimate production of a mechanically-stable open-cell or closed-cell porous foam.

While low vacuum pressures (in the range of 0.90–0.1 atm) may be applied to facilitate the initial evaporation to produce a concentrated, viscous solution, much higher vacuum pressures (0–24 Torr) are used to cause boiling. The vacuum for the boiling step is preferably 0–10 Torr, and most preferably less than about 4 Torr. Boiling in this context means nucleation and growth of bubbles containing water vapor, not air or other gases. In fact, in some solutions, it may be advantageous to purge dissolved gases by application of low vacuum at room temperature. Such "degassing" may help to prevent the solution from erupting out of the drying vessel. Once the solution is sufficiently concentrated and viscous, high vacuum can be applied to cause controlled boiling or foaming. Concentration of the protectant molecules recited above, in the range of 5–70% by weight, during initial evaporation aids in preventing freezing under subsequent high vacuum and adds to the viscosity, thereby facilitating foaming but discouraging uncontrolled eruptions.

Rapid increases in pressure or temperature could cause a foam to collapse. In this case, to enhance the mechanical stability of the porous structures, surfactants may be added as long as those additives do not interfere with the biological activity of the solute intended for conversion to dry form. Moreover, drying of the protectant polymers also contributes to the mechanical stability of the porous structures. Foams prepared according to the present invention may be stored under vacuum, dry gas, like $N_2$ atmosphere and/or chemical desiccant, prior to secondary drying or subsequent vitrification, or before being subdivided or milled, or rehydrated in order to restore their original biologic activity.

Once the invention of combining drying protocols with boiling at reduced pressure is appreciated, it may be seen that in its simplest embodiments the inventive apparatus is a combination of a vacuum pump with a temperature controlled desiccator device. Optional features of such a combination include sensors for temperature and hydrostatic pressure measurements, heat and vacuum (in the range of 0–24 Torr) controls, as well as microprocessors for calculating other process parameters based on data collected from these and other sensors, etc. Such a device allows implementation of a novel two-dimensional vacuum and temperature protocol for drying.

The following working examples illustrate the formation of the mechanically-stable porous foam:

(1) An aqueous 50% glycerol isocitrate dehydrogenase solution from Sigma Chemical Co. containing 59.4 units of activity per ml was dialyzed for 5 hours in 0.1 M TRIS HCl buffer (pH 7.4). The activity of the isocitrate dehydrogenase in the 0.1 M TRIS HCl solution after dialysis was 26±1.8 units per ml. The activity decrease was associated with a decrease in the enzyme concentration because of dilution during the dialysis.

One hundred (100) $\mu$l of the mixture containing 50 ul of 50% by weight sucrose solution and 50 ul of the isocitrate dehydrogenase suspension in 0.1 M TRIS HCl buffer (pH 7.4) was placed in 1.5 ml plastic tubes and preserved by drying at room temperature. First, the samples were dried for 4 hours under low vacuum (0.2 atm). Second, the samples were boiled during 4 hours under high vacuum (<0.01 atm). During this step, a mechanically-stable dry foam was formed in the tubes. Third, the samples were stored during 8 days over DRIERITE under vacuum at room temperature.

After 8 days, the samples were rehydrated with 500 $\mu$l water. Rehydration of the samples containing dry foams was an easy process that was completed within several seconds. The reconstituted sample was assayed for activity by assaying ability to reduce NADP, measured spectrophotometrically at 340 nm. The reaction mix included: 2 ml 0.1 M TRIS HCl buffer, pH 7.4; 10 ul of 0.5% by weight NADP+; 10 $\mu$l of 10 Mm $MnSO_4$; 10 ul of 50 Mm 1-isocitrate; and 10 $\mu$l of an isocitrate dehydrogenase solution. The activity was 2.6±0.2 units/ml, which means there was no loss of activity during drying and subsequent storage at room temperature.

(2) A mixture (100 $\mu$l) containing 50 ul of 50% by weight sucrose and 50 $\mu$l of an ice nucleating bacteria suspension, (INB) Pseudomonas Syringae ATCC 53543, were placed in 1.5 ml plastic tubes and preserved by drying at room temperature. First, the samples were dried for 4 hours under low vacuum (0.2 atm). Second, the samples were boiled during 4 hours under high vacuum (<0.01 atm). After boiling under high vacuum, a mechanically-stable porous structure was formed. Third, the samples were stored during 8 days over DRIERITE under vacuum at room temperature.

After 8 days, the samples were rehydrated with 500 ul water. Rehydration of the samples containing the dry foams was an easy process that was completed within several seconds. Then the samples were assayed for ice nucleation activity in comparison with control samples. We found that there was no significant difference between the ice nucleating activity per 1,000 bacteria in the samples preserved by the present method versus the control samples.

(3) A sample containing 1:1 mixture of concentrated suspension of ice nucleating bacteria (INB) Pseudomonas Syringae ATCC 53543 and sucrose has been used. The sample was mixed until all sucrose crystals were dissolved, so that the final suspension contained 50 wt % sucrose. The suspension was placed in 20ml vials. 2 g of the suspension was placed inside each vial. The vials were dried inside vacuum chamber. The vials were sitting on the surface of a stainless steel shelf inside the chamber. The shelf temperature was controlled by circulating ethylene glycol/water antifreeze at a controlled temperature inside the shelf. Before the vacuum was applied the shelf temperature was decreased to 5° C. Then, the hydrostatic pressure inside the chamber was decreased to 0.3 Torr. Under these conditions the suspension boiled 30 min. The temperature of the shelf was slowly (during 30 min) increased up to 25° C. Visually stable dry foams inside the vials under these experimental conditions were formed within 3 hours. After that the samples were kept under the vacuum at room temperature for one more day. Ice nucleating activity of preserved INB was measured after the sample rehydration with 10 ml of 0.01M phosphate buffer. Ice nucleating activity was measured as a concentration of ice nucleating centers that can nucleate an ice crystal in a 10ul buffer drop during 5 min. at −5° C. The results of the assay show ice nucleating activity in the preserved samples fresh controls.

(4) A concentrated INB suspension was frozen to −76° for future use. 6g of the frozen suspension was melted at 4° C. and mixed with 4 g of 9:1 sucrose: maltrin mixture. The sample was mixed until the sugars were completely dissolved, so that the final suspension contained 35 wt % sucrose and 4 wt % maltrin. The suspension was placed inside 20ml vials. 2 g of the suspension was placed inside each vial. The vials were dried inside a vacuum chamber. The vials were sitting on the surface of stainless steel shelf inside the chamber. The shelf temperature was controlled by circulating ethylene glycol/water antifreeze at a controlled temperature inside the shelf. Before the vacuum was applied the shelf temperature was decreased to 5° C. The hydrostatic pressure inside the chamber was then decreased to 0.5 Torr. Under such a conditions the suspension boiled 30 min. The temperature of the shelf was then slowly (during 30 min) increased up to 25° C. Visually, the formation of stable dry foams inside the vials under these experimental conditions was completed within 2.5 hours. Several vials were removed from the vacuum chamber and the chamber was vacuumed again. After that the temperature was increased to 50° C. and the remaining samples were kept under vacuum during 7 days.

Ice nucleating activity of preserved INB was measured after the sample rehydration with 10 ml of 0.01M phosphate buffer. Ice nucleating activity was measured as a concentration of ice nucleating centers that nucleate an ice crystal in a 10ul buffer drop during 5 min. at −5° C.

We found that ice nucleating activity of the samples that had been removed from the vacuum chamber after drying at 25° C. was approximately 50% from the initial activity of frozen-thawed INB. (The relative standard error in the measurement of ice nucleating activity is less than 20%). Because, it is known that freezing of INB does not significantly decrease ice nucleating activity, the 50% decrease of the activity observed in this experiment is probably because the additional freezing step increases sensitivity of INB to preservation by drying. At the same time, we did not observe additional decrease of the activity of the INB after an additional 7 days drying at 50° C. under vacuum.

(5) 1 ml of 60 wt % sucrose solution was drive 20 ml glass vials inside a vacuum chamber. The vials were sitting on the surface of a stainless steel shelf inside the chamber. The shelf temperature was controlled by circulating ethylene glycol/water antifreeze at a controlled temperature inside the shelf. The temperature of the shelf in this experiment was kept at 20° C. The hydrostatic pressure inside the chamber was kept equal to 0.3 Torr. Under such conditions the solution slowly boiled forming a foam consisting of thin films containing concentrated sucrose in the amorphous state. It takes 2 to 3 hours to form visually stable dry foams inside the vials under these experimental conditions.

(6) Freezer-dried samples of Urokinase were rehydrated with 2 ml of 40wt % sucrose. The solutions were then transferred to 20 ml sterilized glass vials for future preservation by drying. Before drying, the vials were covered with gray slotted rubber stoppers. The vials were dried inside a vacuum chamber. The vials were sitting on the surface of a stainless steel shelf inside the chamber. The shelf temperature was controlled by circulating ethylene glycol/water antifreeze at a controlled temperature inside the shelf. Before the vacuum was applied the shelf temperature was decreased to 5° C. Then the hydrostatic pressure inside the chamber was decreased to 0.5 Torr. Under such a conditions the suspension boiled 30 min. The temperature of the shelf was slowly increased up to 25° C. during 30 min. Visually, stable dry foams inside the vials under these experimental conditions were formed during 3 hours. After an additional 12 hours of drying at room temperature, the temperature was increased to 45° C. for an additional 24 hours. After that the chamber was filled with the dry $N_2$ gas, the rubber stoppers were pushed down and the vials were sealed with aluminum crimped seal.

The samples were assayed right after drying and after 30 days of storage at 40° C. After drying the Urokinase, activity was 93% of the initial activity. This decrease was associated with the loss of Urokinase during transformation from initial vials to the vials at which the Urokinase was dried. After 30 days of storage at 40° C. the activity was 90%. In other words, no additional significant decrease of Urokinase activity during a month of storage at 40° C. was observed.

(7) Freeze-dried samples of Amphotericine B were rehydrated with 5 ml 40wt % sucrose per vial. Then the solutions were transferred into 50 ml sterilized glass vials for future preservation by drying. Before drying, the vials were covered with gray butyl slotted rubber stoppers. The vials were dried inside a vacuum chamber. The vials were sitting on the surface of a stainless steel shelf inside the chamber. The shelf temperature was controlled by circulating ethylene glycol/water antifreeze at a controlled temperature inside the shelf. Before the vacuum was applied the shelf temperature was decreased to 5° C. The hydrostatic pressure inside the chamber was decreased to 0.5 Torr. Under such a conditions the suspension boiled 30 min. The temperature of the shelf was then slowly (during 30 min) increased to 25° C. Visually, stable dry foams inside the vials under these experimental conditions were formed after 3 hours. After an additional 12 hours of drying at room temperature, the chamber was filled with the dry $N_2$ gas and the rubber stoppers in a portion of the vials were pushed down. The vials were removed from the chamber and subsequently sealed with aluminum crimped seal. The samples were assayed right after drying and after 30 day of storage at 27.50 and 40° C. The results are shown in Table 1, together with the results obtained in the next experiment.

Another set of freeze-dried samples of Amphotericin B were rehydrated with 5 ml 40wt % sucrose per vial. The solutions were then transferred into sterilized glass vials for future preservation by drying similar to that described above with additional drying at 45° C. for additional 24 hours. After that, the chamber was filled again with the dry $N_2$ gas, the rubber stoppers were pushed down and the vials were sealed. The samples were assayed right after drying and after 30 day of storage at 27.50 and 40° C. The results are shown in Table 1.

TABLE 1

| | Potency of Amphotericin (%) | | |
| --- | --- | --- | --- |
| | After drying | After 30 days of storage at 27.5° C. | After 30 days of storage at 40° C. |
| Td = 25° C. | 108 | 114 | 95 |
| Td = 45° C. | 103 | 102 | 104 |
| Freeze-dried control | 126 | N/A | N/A |

Where Td is the maximum temperature during drying.

The decrease of Amphotericin activity right after drying was associated with the loss of Amphotericin during transformation from initial vials to the vials at which the Amphotericin was dried. The results of the assay (Table 1) showed that the potency loss was only detected in the samples with maximum temperature during drying at 25° C. while stored at 40° C. which is in agreement with our claims.

(8) A 1.5 ml tube containing a frozen (−76° C.) suspension of *E. Coli* (Epicurian Coli XL10-GOLD) from Stratagene was thawed in an ice bath. A 100μl aliquot was transferred to 50 ml of NZYM (Case in digest yeast extract medium) broth and incubated at 37° C. on an orbital shaker over night. After 14 hours of growth, 10 ml of this growth culture was inoculated into 100ml of sterile NZYM broth to continue the culture growth at 37° C. During the culture growth the optical density (OD@620nm) was measured every hour to determine the end of Logarithmic bacteria growth. When the transition phase was reached (OD=1 to 1.06) the cells were ready to be harvested. 5ml of the culture was pipetted into a centrifuge tube and centrifuged for 10 minutes. then the supernatant was poured off and the weight of the pellets were measured to determine the approximate concentration of the cells.

Figure 3:
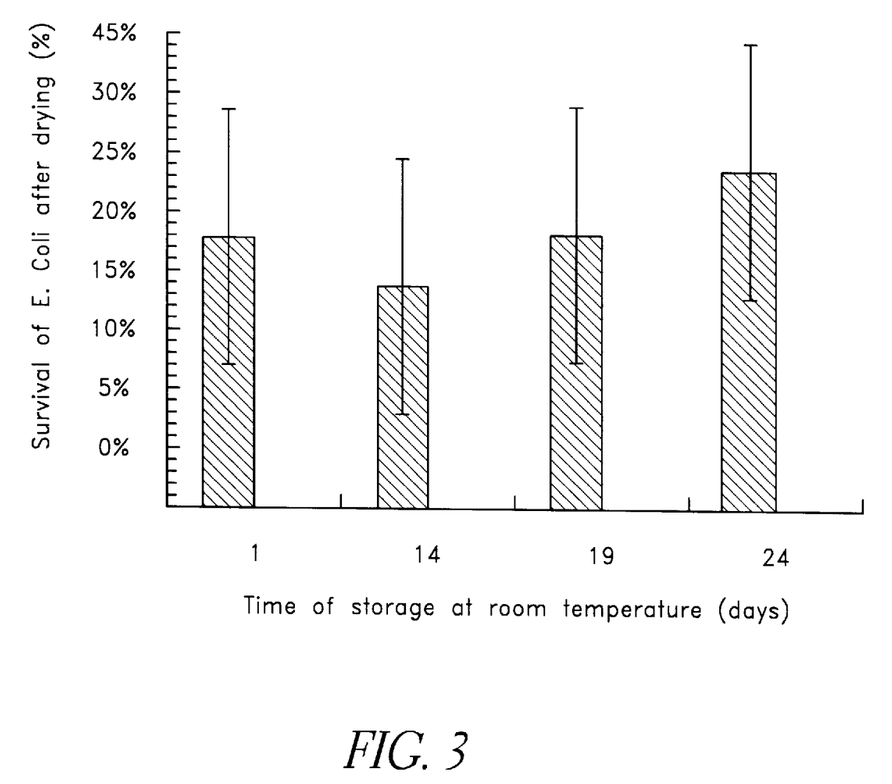
FIG. 3 is a graph depicting survival of dried *E.Coli* as a function of storage time at room temperature.

The cells were re-suspended with 5ml of NZYM broth or preservation solution consisting of 25% sucrose and 25% fructose in MRS broth. The cells re-suspended with NZYM broth were used as a control. 1ml of cells re-suspended with 25% sucrose and 25% fructose in MRS broth were placed in 20 ml glass vials and dried under vacuum similar to the INB were dried in the example #2. After that, the samples were kept under the vacuum up to 24 days at room temperature. Dried samples were assayed at selected time intervals. The survival of the preserved cells were measured after rehydration with 0.1% peptone solution in water at room temperature. To determine concentration of viable cells the suspensions were pour plated in Petri dishes at the appropriate dilution on LB Miller agar followed by incubation at 37§ eC for 36–48 hours. We found that 25±10% of control cells survived after drying and one day of storage under vacuum. We also found that this same portion of these survived cells did not decrease during subsequent 24 days of storage under vacuum at room temperature (FIG. 3).

Partially dehydrated samples or mechanically-stable foams, already stabilized by primary drying, may undergo secondary drying at increased temperatures. Since Tg is dependent on the water content of the sample and since Tg increases with increased dehydration, different secondary drying protocols may be applied depending on the desired storage temperature, to generate a Tg consistent with vitrification upon cooling to that storage temperature. However, because dehydration of materials is practically impossible once they have entered the glass state, the key to vitrification according to the present invention, where ambient storage temperatures may be desired, is to conduct the dehydration at a temperature significantly higher than the ambient temperature.

Storage temperatures are preferably within the range of 0°–70° C. More preferably, common storage temperature selections are greater than or equal to 0°, 4°, 20°, 40°, and 50° C. Implementing the vitrification protocol in some cases, where refrigerated storage is selected, may require only dehydration at room temperature followed by cooling to below room temperature for refrigerated storage. In other instances, however, where stability at ambient temperatures is desired, dehydration at a temperature above room temperature should be employed, followed by cooling to room temperature.

For any given specimen to be preserved, the nature and stability characteristics of the specimen will determine the maximum temperature it can withstand during the primary drying step. In the case of enzyme preservation, it was shown that after primary drying at room temperature the secondary drying temperature may be increased up to 50° C. without loss of enzymatic activity. Then, the dehydration process can be continued during secondary drying at higher temperature. Thus, by continuous or step-wise simultaneous increase of the extent of dehydration and dehydration temperature, labile proteins can be placed in a state of thermal stability at temperatures well above their denaturation temperature.

In addition to conducting the secondary drying at a temperature above the selected storage temperature, it is critical that this drying is carried out for a period of time sufficient to actually raise Tg above the storage temperature. Based on empirical results using a sucrose-raffinose mixture (FIG. 2), it was demonstrated that more than 12 hours of secondary drying at temperatures above 70° C. was required to raise Tg to above 25° C. Primary drying in these experiments was for 12 hours at room temperature (20° C). The results suggest that extended secondary drying times (more than 12 hours at 70° C. and more than 36 hours at 50° C.) may be needed to effect increases in Tg over room temperature. For some biological materials which are not heat labile, primary drying at higher temperatures, would reduce the secondary drying time at elevated temperatures needed to increase Tg to above the selected storage temperature.

To insure that the Tg is actually greater than the storage temperature, at least two methods are known for estimating Tg by thermal analysis. Differential scanning calorimetry (DSC) is the most commonly used technique. However, DSC is unreliable for measuring Tg in samples which contain polymers (FIG. 1). Alternatively, Thermally Stimulated Depolarization Current (TSDC) methods are specifically adapted for analysis of polymers. The TSDC method is preferred because it is reliable for all samples, although it requires slightly larger sample volumes.

While vitrification may increase the time of dissolution in water or rehydrating solution, which in itself may cause certain damage to some specimens in some cases, this unwanted effect may be ameliorated by judicious heating of the rehydration solution prior to its application to the vitrified specimen. Heating is judicious when it is controlled within the limits which minimize sample damage. However, some samples may gain increased stability by rehydration at lower temperatures.

Although the invention has been described in detail for the purposes of illustration, it is understood that such detail is solely for that purpose, and variations can be made therein by those skilled in the art without departing from the spirit and scope of the invention which is defined by the following claims.

What is claimed is:

1. A scalable method for preservation of a vaccine, comprising:

forming a suspension by adding to said vaccine a protectant comprising a disaccharide and a methylated monosaccharide; and boiling said suspension under vacuum at a temperature of −15° C. to 70° C. to form a mechanically-stable foam.

2. The method of claim 1, wherein prior to boiling, said suspension is concentrated by freeze-drying.

3. The method according to claim 1, wherein prior to boiling, said suspension is degassed under reduced atmospheric pressure.

4. The method according to claim 1, wherein said disaccharide is sucrose.

5. The method according to claim 1, wherein said protectant comprises sucrose and methyl α-d-glucopyranoside.

6. A scalable method for preservation of a vaccine, comprising:

forming a suspension by adding to said vaccine a protectant comprising a disaccharide and a methylated monosaccharide;

boiling said suspension under vacuum at a temperature of −15° C. to 70° C. to form a mechanically-stable foam;

drying said mechanically-stable foam at a temperature greater than a selected storage temperature, and for a time sufficiently long to raise the vaccine's glass transition temperature above the selected storage temperature; and cooling said mechanically-stable foam to the selected storage temperature.

* * * * *